(12) United States Patent
Kim

(10) Patent No.: US 10,653,541 B2
(45) Date of Patent: May 19, 2020

(54) STENT DELIVERY ASSEMBLY

(71) Applicant: Cook Medical Technologies LLC, Bloomington, IN (US)

(72) Inventor: Woong Kim, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 81 days.

(21) Appl. No.: 15/807,658

(22) Filed: Nov. 9, 2017

(65) Prior Publication Data

US 2018/0168837 A1 Jun. 21, 2018

Related U.S. Application Data

(60) Provisional application No. 62/437,076, filed on Dec. 21, 2016.

(51) Int. Cl.
| A61F 2/958 | (2013.01) |
| A61F 2/82 | (2013.01) |
| A61F 2/915 | (2013.01) |

(52) U.S. Cl.
CPC .............. *A61F 2/958* (2013.01); *A61F 2/915* (2013.01); *A61F 2002/825* (2013.01); *A61F 2002/91575* (2013.01); *A61F 2002/9583* (2013.01); *A61F 2210/0061* (2013.01)

(58) Field of Classification Search
CPC .......................... A61F 2/958; A61F 2002/9583
See application file for complete search history.

(56) References Cited

U.S. PATENT DOCUMENTS

| 5,628,730 A | 5/1997 | Shapland et al. |
| 5,746,745 A * | 5/1998 | Abele ................... A61F 2/958 604/103.08 |
| 6,231,600 B1 | 5/2001 | Zhong |
| 6,364,856 B1 | 4/2002 | Ding et al. |
| 6,364,893 B1 | 4/2002 | Sahatjian et al. |
| 8,153,181 B2 * | 4/2012 | Holman ................. A61F 2/958 427/2.1 |
| 2004/0044404 A1 | 3/2004 | Stucke et al. |
| 2005/0106206 A1 | 5/2005 | Herweck et al. |
| 2006/0265040 A1 * | 11/2006 | Murray .................. A61F 2/958 623/1.11 |
| 2009/0177267 A1 * | 7/2009 | Biggs ........................ A61F 2/86 623/1.17 |
| 2012/0089218 A1 * | 4/2012 | Dardi ....................... A61F 2/07 623/1.15 |

(Continued)

*Primary Examiner* — Sarah A Simpson
(74) *Attorney, Agent, or Firm* — Brinks Gilson & Lione

(57) ABSTRACT

A stent delivery assembly includes a delivery balloon defining a balloon axis, and a stent disposed around the delivery balloon. The stent has interconnected struts, and the delivery balloon has a balloon surface with a number of strips that are disposed on the balloon surface and extend along the balloon axis, the strips having an unhydrated state and a hydrated state, the strips having a smaller volume in the unhydrated state than in the hydrated state. For a stent composed of axially aligned segments connected via connectors disposed between adjacent ones of the segments, the strips have a length greater than an axial distance between axially outermost connectors connecting the adjacent ones of the segments.

14 Claims, 3 Drawing Sheets

(56) References Cited

U.S. PATENT DOCUMENTS

2013/0178928 A1* 7/2013 Vyas .................. A61F 2/915
                                                   623/1.16
2016/0030165 A1* 2/2016 Mitra ................. A61F 2/2409
                                                   623/2.42

* cited by examiner

US 10,653,541 B2

STENT DELIVERY ASSEMBLY

TECHNICAL FIELD

The present application deals with a stent delivery assembly, in particular a stent delivery assembly including a delivery balloon.

BACKGROUND

A stent is a generally cylindrical prosthesis introduced via a catheter into a lumen of a body vessel in a collapsed configuration having a generally reduced diameter and then expanded to the diameter of the vessel. In the expanded configuration, the stent supports and reinforces the vessel walls while maintaining the vessel in an open, unobstructed condition. Stents may be self-expanding or balloon-expandable. Balloon expandable stents are expanded by placing the stent on a deflated balloon catheter and by inflating the delivery balloon at the location where the stent is to be placed.

It has been observed that, during the inflation of the delivery balloon, the stent may shift. Segmented stents have segments configured to detach from one another to allow for independent expansion of each segment, especially in vessels having significantly varying cross-sections in the implant location. During the delivery and inflation process, these segments might additionally shift relative to one another.

SUMMARY

According to a first aspect of the present application, a stent delivery assembly includes a delivery balloon having a balloon axis and a balloon surface with a number of strips disposed on the balloon surface and extending along the balloon axis. The strips have an unhydrated state and a hydrated state with a smaller volume in the unhydrated state than in the hydrated state.

According to another aspect of the invention, the strips are made of a material that in the hydrated state reacts to deformation with an elastic force. For example, the material may be selected from a hydrogel, an expandable foam, or an expandable elastomer.

According a further aspect of the invention, the delivery balloon may have a pleated collapsed state with a number of pleats, the number of pleats being identical to the number of strips. Each pleat may include one outer fold with one of the strips being disposed on or adjoining the fold.

According to yet another aspect of the invention, the delivery balloon in the collapsed state has a collapsed circumference and each of the number of strips has a circumferential width that is at most equal to the collapsed circumference divided by the number of strips. For example, the number of pleats may be in a range of 3 through 12.

According to another aspect of the invention, each strip has a volume that at least doubles from the unhydrated state to the hydrated state.

According to a further aspect of the invention, the stent delivery assembly may further include a stent disposed around the delivery balloon. The struts of the stent have a strut thickness and the strips have a thickness in the unhydrated state that may be less than the strut thickness. Further, the strips have a thickness in the hydrated state that may be at least equal to the strut thickness.

According to yet another aspect of the invention, during a hydration of the strips, the strips exert a radially outward force on the stent that is smaller than a force required to expand the stent.

According to a further aspect of the invention, the stent is composed of axially aligned segments connected via connectors disposed between adjacent ones of the segments, wherein the strips have a length greater than an axial distance between axially outermost connectors connecting the adjacent ones of the segments.

Further details and benefits will become apparent from the following detailed description of the accompanying drawings. The drawings are provided for purely illustrative purposes and are not intended to limit the scope of the present invention.

DETAILED DESCRIPTION OF THE DRAWINGS

Figure 1:
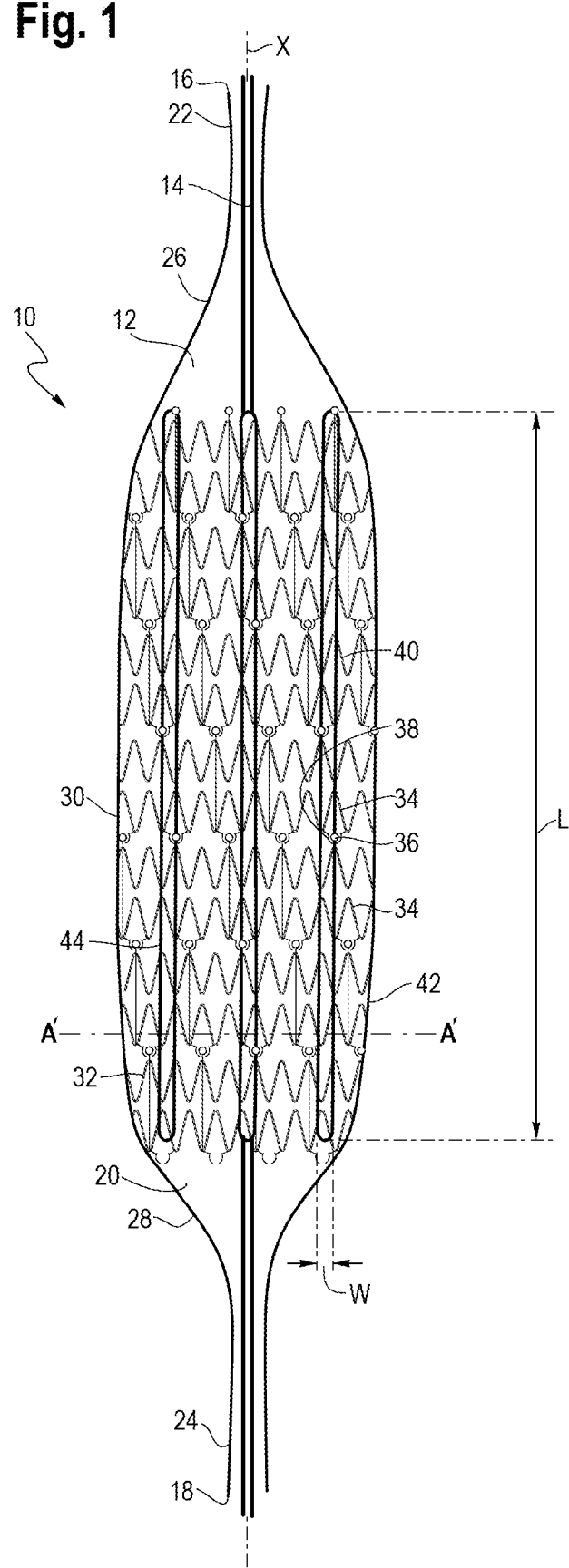
FIG. 1 shows a stent delivery assembly including a delivery balloon and a stent in an expanded configuration prior to delivery.

Referring to FIG. 1, a stent delivery assembly 10 is shown in an expanded state. The stent delivery assembly 10 includes a stent delivery balloon 12 surrounding an inner tube 14 that defines a longitudinal axis X and extends beyond a proximal end 16 of the delivery balloon 12 on one side and beyond a distal end 18 of the delivery balloon 12 on the other side. An inflation lumen for delivering saline solution into the annular space 20 surrounding the inner tube 14 in the interior volume of the delivery balloon 12 may be formed as a second lumen inside the inner tube 14 with a radial opening into the annular space 20. Alternatively, the proximal end 16 of the delivery balloon 12 may be affixed to an outer tube (not shown) that terminates in the annular space 20. Generally, any known arrangement to inflate the delivery balloon 12 is suited for obtaining the benefits of the present disclosure.

The delivery balloon 12 is composed of generally five sections 22, 24, 26, 28, and 30. At the proximal end 16, the delivery balloon 12 includes a proximal attachment neck 22 for sealingly affixing the proximal end 16 to the inner tube 14 (or to the outer tube if present). At the distal end 18, the delivery balloon 12 includes a distal attachment neck 24 for sealingly affixing the distal end 18 to the inner tube 14.

Adjacent to the proximal attachment neck 22, the delivery balloon 12 includes a proximal tapered portion 26, and adjacent the distal attachment neck 24, the delivery balloon 12 includes a distal tapered portion 28. Each tapered portion has an increasing circumference with increasing distance from the respective adjacent proximal attachment neck 22 or distal attachment neck 24.

Centrally arranged between the proximal tapered portion 26 and the distal tapered portion 28, the delivery balloon 12 includes a tubular central portion 30 connecting the proximal tapered portion 26 and the distal tapered portion 28.

The central portion 30 carries a tubular, radially expandable stent 32 forming an arrangement of struts 40. Without limitation, the stent 32 may be of a one-piece construction or a segmented stent 32 formed from axially aligned tubular segments 34. The segments 34 may be connected in the collapsed state via male connectors 36 engaging female connectors 38 between neighboring stent segments 34. The male and female connectors 38 may open up during the expansion of the stent 32 to release the male connectors 36 and to disconnect neighboring segments 34 from one another.

Along the central portion 30, the surface of the delivery balloon 12 carries a plurality of strips 44 extending parallel to the axis X. The strips 44 are durably attached to the balloon surface 42 by an adhesive, heat bonding or coextrusion, depending on the materials of the balloon surface 42 and of the strips 44. The strips 44 are made of an expandable material, for example of an expandable foam or sponge, hydrogel, or an elastomer, such as silicone or polyurethane rubber. A sponge, for example may be dried in a compressed shape so that it will expand when hydrated. The strips 44 swell up and increase their volume upon exposure to a liquid, such as a bodily fluid. Because the strips 44 are secured to the balloon surface 42 in two dimensions, it is primarily the third, radial, dimension that grows from the contact with the liquid. In the hydrated state, the strips 44 have a thickness T at least equal to the thickness D of the struts 40 of the stent.

While the length L of the strips 44 may generally be about equal to the length the central portion 30 of the delivery balloon 12, they may extend partially into the proximal tapered portion 26 and the distal tapered portion 28 without departing from the present invention. Also, while the strips 44 may be shorter than the length of the central portion 30 of the delivery balloon 12, the function of inhibiting microsliding is greatly improved if the strips 44 extend at least over an axial length that includes all stent connectors 36 and 38 between adjacent segments 34.

Figure 2:
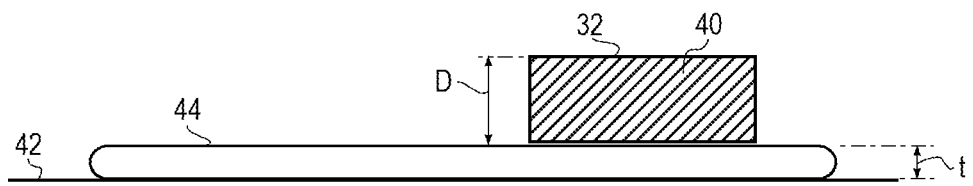
FIG. 2 shows a close-up detail of FIG. 1.

As can be seen from the close-up detail view of FIG. 2, the strips 44, in their unhydrated, compressed state before exposure to fluid, may have a thickness t that is smaller than the radial thickness D of the struts 40 of the stent 32. Thinner strips 44 produce less bulk than thicker strips 44 in the crimped compressed configuration, in which the collapsed delivery balloon 12 carrying the collapsed stent is introduced into the implant location via a delivery sheath. In the shown example, the strips 44 in their unhydrated state have a greater firmness than in their hydrated state shown in FIGS. 3 and 4 so that the stent stays on top of the radially outer surface 46 of the strips 44 in the unhydrated state.

Figure 3:
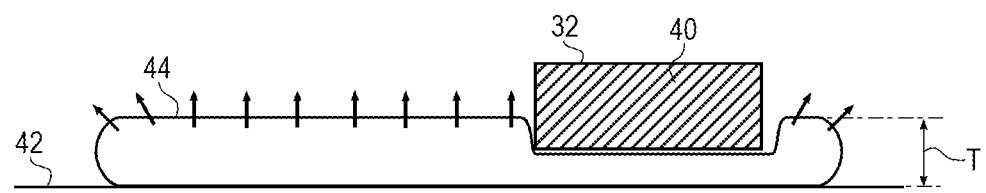
FIG. 3 shows the close-up detail of FIG. 2 in a hydrated condition after exposure to a liquid, for example bodily fluid.

Upon hydration of the strips 44, FIG. 3 shows how the strips 44 expand where the radially outer surface 46 is exposed to fluid. The strips 44 swell up to a hydrated thickness T, which is at least twice their unhydrated thickness t, from the unhydrated state to the hydrated state. In the hydrated state, the thickness T of the strips 44 may be equal to or greater than the thickness D of the struts 40. As the stent struts 40 locally constrain the expansion of the strips 44 in locations where the stent 32 contacts the outer surface 46, these locations do not swell up to the same extent as locations absent such constraint, even if the fluid reaches the constrained locations. Generally, the radial force that the strips 44 exert on the stent 32 during hydration is smaller than the force required to expand the stent 32. Accordingly, the stent struts 40 cause indentations in the hydrated strips 44 as shown in FIG. 3, and the strips 44 mold themselves around the stent struts 40.

The hydration occurs as soon as the strips 44 come into contact with bodily fluid, thus before the stent 32 reaches the implant location. By the time the stent 32 is delivered to its destination, the strips 44 are already hydrated and have molded themselves to the stent struts 40. Accordingly, the stent 32 is secured on a customized bed 50.

Figure 4:
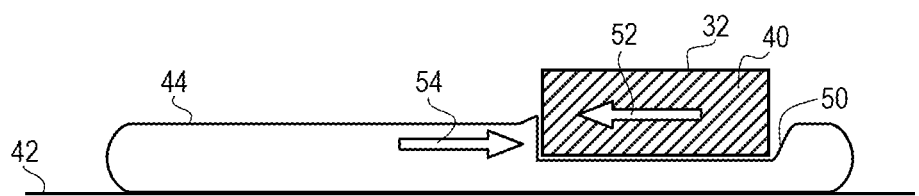
FIG. 4 shows the close-up detail of FIG. 3 reacting to a microsliding force.

FIG. 4 illustrates forces exerted on the stent 32 and on the strips 44 during balloon expansion from the right side of FIG. 4. Assuming that the balloon diameter increases from the right, the balloon surface 42 becomes sloped toward the balloon axis X from the right to the left side in the view of FIG. 4. As the stent 32 resists expansion, a downhill force toward the left acts on the stent 32. Absent any resistance, the stent 32 would slide to the left by microsliding as indicated by arrow 52. As such a movement, however, digs the stent 32 into the hydrated strips 44, the strips 44 resist the deformation and react with a counterforce 54 toward the right. In addition to being a frictional force, the counterforce is also an elastic force caused by the deformation of the hydrated strip. This is of particular interest for segmented stents 32. The individual stent segments 34 undergo locally different forces so that the segments may be shifted relative to one another absent any restraint. The strips 44 greatly reduce the risk of microsliding by providing the counterforce to the movements of the segments.

Figure 5:
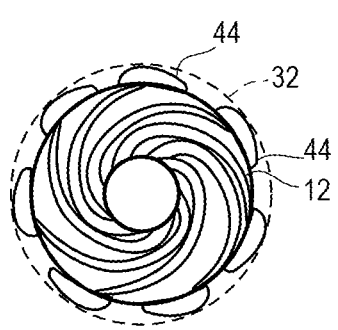
FIG. 5 shows the delivery assembly of FIG. 1, but in a collapsed configuration in the cross-section A'-A'.
Figure 6:
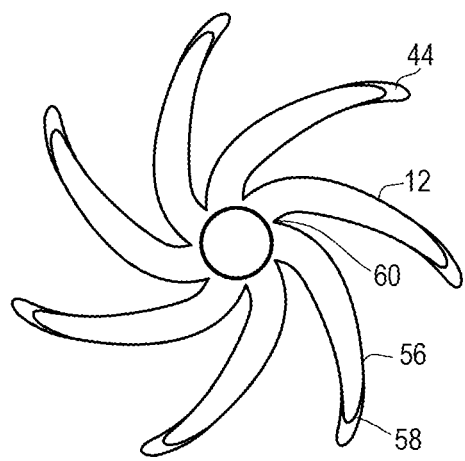
FIG. 6 shows the delivery balloon of FIG. 1 in a partially expanded configuration in the cross-section A'-A'.
Figure 7:
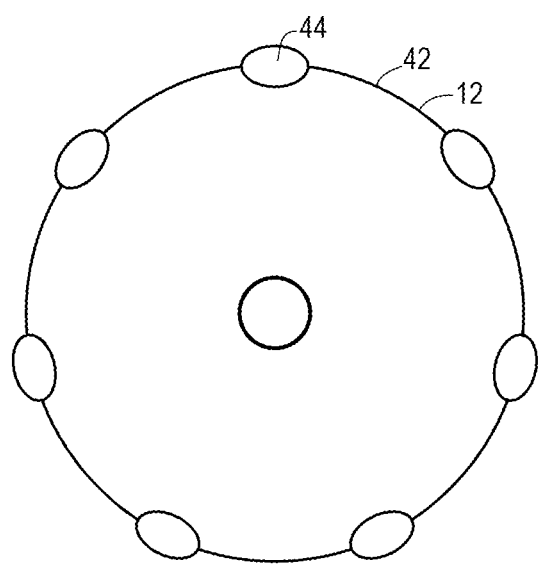
FIG. 7 shows the delivery balloon of FIG. 1 in a the expanded configuration prior to exposure to liquid in the cross-section A'-A'.
Figure 8:
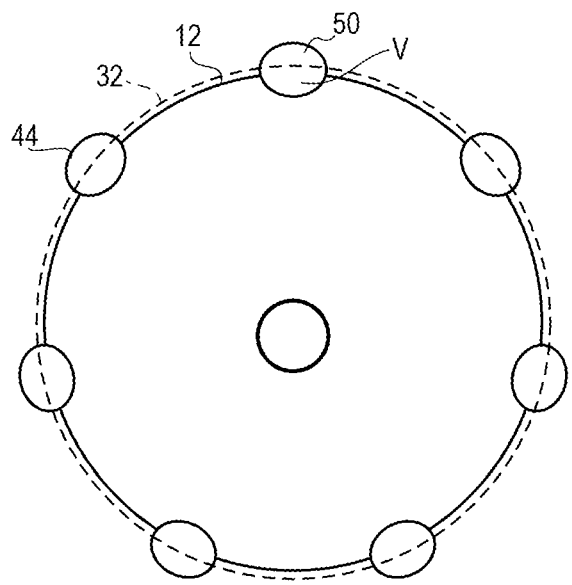
FIG. 8 shows the delivery assembly of FIG. 1 in a the expanded configuration in the hydrated condition in the cross-section A'-A'.

FIGS. 5 through 8 show the delivery balloon 12 at different stages of expansion. Notably, the stages shown in FIGS. 6 and 7 do not correspond to delivery stages of the stent delivery assembly 10 because the strips 44 swell up prior to expanding the delivery balloon 12 when the stent delivery assembly 10 is introduced to a delivery location. FIGS. 5 and 8, however, show stages of the stent delivery assembly 10 during implantation of the stent 32.

Now referring to FIG. 5, the delivery balloon 12 is in a collapsed state. In FIG. 5, the stent 32 positioned on the delivery balloon 12 is schematically indicated by a broken circle. The delivery balloon 12 is folded into pleats 56, with the same number of outer folds 58 carrying the strips 44 and inner folds 60 free of strips 44. The term "pleat" is used in this context is used to designate a balloon portion extending between two adjacent inner folds 60. Thus, a pleat 56 as defined herein has two sides folded toward each other via an outer fold 58.

FIG. 6 shows a partially unfolded balloon for illustrating the locations of the strips 44. The number of strips 44 equals the number of pleats 56, and one of the strips 44 is located at the outer fold 58 of each pleat 56. While FIG. 6 shows the outer folds 58 covered by the strips 44, the outer folds 58 may alternatively form a lateral edge of the strips 44 so that the strips 44 are arranged on the side of the pleat 56 that faces outward in the collapsed state. For example, in FIG. 6, where the pleats 56 are wrapped in the clockwise direction, the strips 44 would be adjoining the outer folds 58 in the counterclockwise direction.

The width W of the strips 44 in the circumferential direction around the balloon axis X is preferably smaller than the circumference of the delivery balloon 12 in the collapsed state divided by the number of pleats 56. For example, the shown balloon has seven pleats 56 and thus seven strips 44. Accordingly, the width of each of the strips 44 should not exceed 1/7 of the circumference of the delivery balloon 12 in the collapsed state shown in FIG. 5. The number of pleats 56 may be varied, depending on the expanded size of the delivery balloon 12. A balloon with a larger circumference may be more conveniently packaged with a greater number of pleats 56 to reduce the depth of each pleat 56 for easier inflation. Accordingly, the number of pleats 56 and strips 44 of the delivery balloon 12 may be in the range of 3 through 12, preferably in a range of 5 through 9. A smaller number than 3 may not provide a sufficient resistance against microsliding of the stent 32 on the delivery balloon 12. A larger number than 12 may require the strips 44 to be very narrow and thus less resilient against the microsliding forces exerted by the stent 32.

FIG. 7 shows the delivery balloon 12 in an expanded state, while the strips 44 are unhydrated. The strips 44 are in their compressed condition and are evenly circumferentially distributed around the balloon axis X. The outer and inner folds 58, 60 have been straightened so that the delivery balloon 12 has a generally circular cross-section. The strips 44 in FIG. 7 are shown as have an oval cross-section in the unhydrated state. The cross-section of the strips 44 may have different shapes, such as rectangular or semi-circular, for example extending only outward from the outer balloon surface 42.

In FIG. 8, the expanded delivery balloon 12 of FIG. 7 is shown with hydrated strips 44. The hydration of the strips 44 has caused the strips 44 to swell up to a greater volume V than in FIG. 7. The volume V of the strips 44 may, for example, be at least doubled compared to the unhydrated state. As mentioned above, the hydrated strips 44 are softer than compressed, unhydrated strips 44. In FIG. 8, the stent 32 is again schematically indicated by a broken circle to illustrate how the stent struts 40 are embedded in the hydrated strips 44. The stent 32 radially overlaps with the hydrated strips 44 that have molded themselves around the stent struts 40 to form the customized bed 50.

But because the hydrated strips 44 do not completely enclose the stent struts 40 on the outside, the delivery balloon 12 can be disengaged from the stent struts 40 by simple deflation. The delivery balloon 12 returns into its pleated state, albeit with hydrated strips 44. As the strips 44 have mostly expanded radially outward, they do not interfere with each other in a circumferential direction to a degree that would inhibit the removal of the delivery balloon 12 from the implantation site.

While the above description constitutes the preferred embodiments of the present invention, it will be appreciated that the invention is susceptible to modification, variation and change without departing from the proper scope and fair meaning of the accompanying claims.

What is claimed is:

1. A stent delivery assembly comprising
a delivery balloon having a balloon axis and a balloon surface with a number of strips durably attached to the balloon surface and extending along the balloon axis, the strips having an unhydrated state and a hydrated state, the strips having a smaller volume in the unhydrated state than in the hydrated state, the strips in the hydrated state being radially indentable and configured to inhibit microsliding of a stent along a surface of the strips by an elastic counterforce, wherein the delivery balloon has a pleated collapsed state with a number of pleats connected to one another via inner folds, the number of pleats being identical to the number of strips, and each pleat having an outer fold, a respective one of the strips being disposed at or on the outer fold and the inner folds being free of strips.

2. The stent delivery assembly of claim 1, wherein the strips are made of a material that in the hydrated state reacts to deformation with an elastic force.

3. The stent delivery assembly of claim 1, wherein the strips are made of a hydrogel.

4. The stent delivery assembly of claim 1, wherein the strips are made of an expandable foam.

5. The stent delivery assembly of claim 1, wherein the strips are made of an expandable elastomer.

6. The stent delivery assembly of claim 1, wherein the delivery balloon in the collapsed state has a collapsed circumference and each of the number of strips has a circumferential width that is at most equal to the collapsed circumference divided by the number of strips.

7. The stent delivery assembly of claim 1, wherein the number of pleats is in a range of 3 through 12.

8. The stent delivery assembly of claim 1, wherein each strip has a volume that at least doubles from the unhydrated state to the hydrated state.

9. A stent delivery assembly comprising
a delivery balloon defining a balloon axis, and
a stent disposed around the delivery balloon,
wherein the stent has interconnected struts and the delivery balloon has a balloon surface with a number of strips that are durably attached to the balloon surface and extend along the balloon axis, the strips having an unhydrated state and a hydrated state, the strips having a smaller volume in the unhydrated state than in the hydrated state, wherein the strips are made of a material that in the hydrated state reacts to deformation with an elastic force that inhibits a microslide of the stent during an expansion of the delivery balloon.

10. The stent delivery assembly of claim 9, wherein the struts of the stent have a strut thickness and the strips have a thickness in the unhydrated state that is less than the strut thickness.

11. The stent delivery assembly of claim 9, wherein the struts of the stent have a strut thickness and the strips have a thickness in the hydrated state that is at least equal to the strut thickness.

12. The stent delivery assembly of claim 9, wherein during a hydration of the strips, the strips exert a radially outward force on the stent that is smaller than a force required to expand the stent.

13. The stent delivery assembly of claim 12, wherein the struts locally constrain the strips as the radially outward force is exerted on the stent during the hydration of the strips, thereby forming an indentation in the strips and securing the stent on a customized bed.

14. The stent delivery assembly of claim 9, wherein the stent is composed of axially aligned segments connected via connectors disposed between adjacent ones of the segments, wherein the strips have a length greater than an axial distance between axially outermost connectors connecting the adjacent ones of the segments.

* * * * *